United States Patent [19]

Ender et al.

[11] 4,055,172
[45] Oct. 25, 1977

[54] NAIL AND SET FOR CORRECTLY RESETTING FRACTURED BONES FOR THEIR IMMEDIATE RE-USE

[76] Inventors: Josef Ender, Steinbrecherring 23,A, 4400 Steyr; Hans-Georg Ender, Ferstelgasse 6/20 A, 1090 Vienna, both of Austria

[21] Appl. No.: 568,987

[22] Filed: Apr. 17, 1975

Related U.S. Application Data

[63] Continuation of Ser. No. 477,418, June 7, 1974, abandoned.

[30] Foreign Application Priority Data

July 18, 1973 Austria .................................. 6344/73

[51] Int. Cl.² .............................................. A61F 5/04
[52] U.S. Cl. ............................. 128/92 BC; 128/92 BA
[58] Field of Search ........... 128/92 BC, 92 B, 92 BA, 128/92 EC, 92 C, 92 D, 92 R, 83

[56] References Cited

U.S. PATENT DOCUMENTS

| 2,998,007 | 8/1961 | Herzog | 128/92 BC |
|---|---|---|---|
| 3,709,218 | 1/1973 | Halloran | 128/92 BC |
| 3,779,239 | 12/1973 | Fischer et al. | 128/92 BC |

FOREIGN PATENT DOCUMENTS

| 960,010 | 10/1949 | France | 128/92 B |
|---|---|---|---|
| 735,333 | 4/1943 | Germany | 128/92 EC |
| 118,595 | 4/1947 | Sweden | 128/92 EC |
| 1,022,328 | 3/1966 | United Kingdom | 128/92 EC |

OTHER PUBLICATIONS

Journal of Bone & Joint Surgery, vol. No. 28, Apr. 1946, p. 313.

Primary Examiner—John D. Yasko
Attorney, Agent, or Firm—Otto John Munz

[57] ABSTRACT

The nail has a proximal driving-and a distal attachment-end-portion and intermediate portions of different shapes, resiliencies, lengths, non-uniform curvatures, bends and thicknesses, designed for driving it through the hollow of the fractured bone and for rotationally correctly resetting the bone in position with optimum ease and efficiency and for holding it fixedly reset until the fracture heals. A matching tool set for the temporary attachment of the proximal end of the nail for the driving, rotation and withdrawal of the nail operations is provided in a package with a plurality of nails of different sizes to be available instantaneously to the surgeon in an emergency.

8 Claims, 19 Drawing Figures

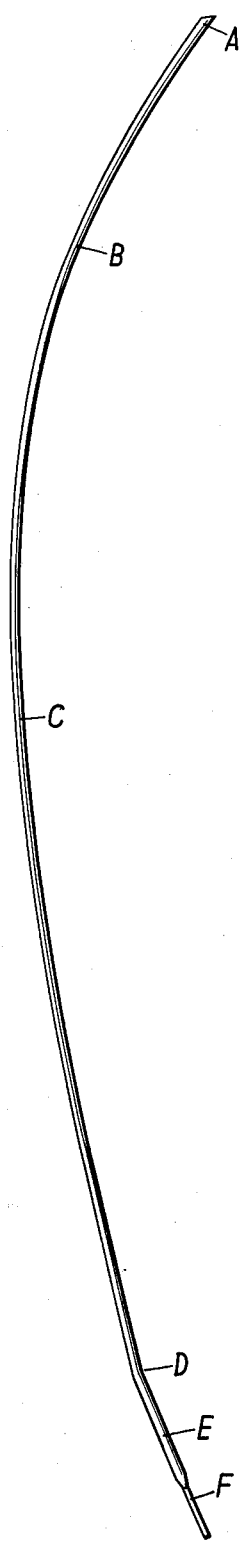
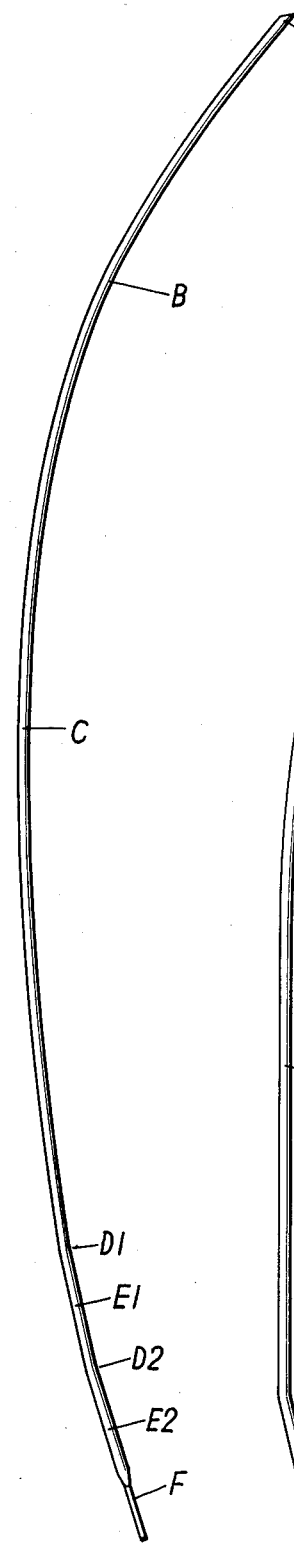
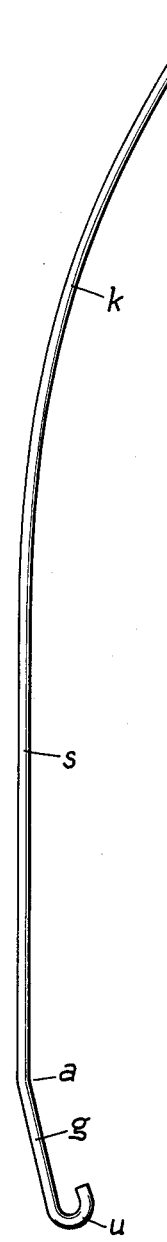
FIG.13a
Qu 1 — 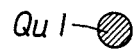
FIG.13b
Qu 2 — 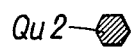
FIG.13c
Qu 3 — 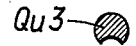
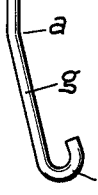

NAIL AND SET FOR CORRECTLY RESETTING FRACTURED BONES FOR THEIR IMMEDIATE RE-USE

This is a streamlined continuation of Application Ser. No. 477,418, filed June 7, 1974, now abandoned.

CROSS-REFERENCE TO RELATED APPLICATIONS

Priority of corresponding Austrian patent application A 6344/73, filed July 18, 1973 under Convention, and the filing date of the corresponding U.S. patent application Ser. No. 477,418 filed June 7, 1974 and abandoned Apr. 22, 1975 are claimed.

FIELD OF THE INVENTION

Surgical device for re-setting fractured bones and a repositioning and fixation of pertrochanterous and subtrochanterous fractures including a package of nails with a matching tool set.

DESCRIPTION OF THE PRIOR ART

Nails are known which are straight throughout their length and which are angled only as they are driven into the femur. It has also been proposed to impart a uniform curvature to the nails.

None of the previously known nails enables a repositioning of the bone fragments from below, without a surgical operation to open the region, and a penetration of the proximal point of the nail into the femur head.

SUMMARY OF THE INVENTION

The objects of the invention are to provide:

a nail which permits the repositioning of bones and the repositioning and fixation of pertrochanterous and subtrochanterous fractures by driving the proximal end of the nail upwardly into the femur head from below, from the medial condyl toward the carnal by a minor surgical operation, involving the precutting of a small hole, and by rotation of the protruding distal end of the driven nail within the hollow of the bone, preferably under X-ray observation, until the fragments are pushed into a perfectly correct alignment and a nail which is endowed with a longitudinal and lateral resiliency and optionally with bends and curves, permitting its easy handling and bending within the hollow of the bone as it is driven in and rotated by a tool mating with its distal end to force it to slide and skid along the inside hollow wall of the bone to reposition the fractures.

This is accomplished according to the invention that the nail is curved in part of its length from its proximal end, said curved portion is succeeded by a straight portion, and the nail is provided at its distal end with a coupling element, which permits of a non-rotatable connection to a driving tool.

The distal portion is suitably provided with a bend, which may be succeeded toward the end by a straight portion.

A second bend is desirable. In that case, the first bend causes the coupling element to be nearer to the bone and the second holds the coupling element away from the bone.

These two bends may be replaced by a continuously curved portion which conforms to the femur condyle.

According to a further feature of the invention, the nail is provided at its distal end with a U-shaped, reversely bent portion, which has a blunt end face, which is engageable by a nail set.

A reverse bend which requires a relatively large space and may be undesirable particularly when a plurality of nails are to be driven can be avoided according to the envention in that the distal portion is flattened or polygonal as an extension of the nail. A flattened portion may be provided with a slot.

The nail has suitably a covering of plastics material.

The invention provides also a nail set, which serves to drive such nail and which is provided with a recess, which conforms to the end of the nail and serves to engage the same; the nail set is sword-shaped, having a cross-member.

BRIEF DESCRIPTION OF THE DRAWINGS

The above-mentioned and further features of the invention will become apparent from the drawing, which are to scale and show embodiments of the invention by way of example.

FIG. 1 is a front elevation showing the nail.

FIG. 2 is a side elevation showing the nail.

FIG. 11 is a front elevation showing a nail, which is a modification of that of FIG. 1.

FIG. 12 shows another embodiment of the nail.

FIG. 13 shows corresponding transverse sectional views.

The nail shown in FIGS. 1 and 2 has a proximal end A, which is beveled at an angle of about 45° and which is succeeded by a steeply curved portion B. The latter merges into a less steeply curved an finally straight portion C. The entire curvature of the nail extends over one-third to two-thirds of its length.

Part C is succeeded by a bend D and a straight portion E. In its last centimeters, the distal portion thus has a large departure toward medial portion and thus holds the end away from the medullary space and the femur condyle. The end portion F of the nail forms a flat plate and is formed with a slot G.

The nail shown in FIG. 11 differs from the nail of FIGS. 1 and 2 in that it has two bends $D_1$ and $D_2$ and two straight portions $E_1$ and $E_2$.

Figure 14:
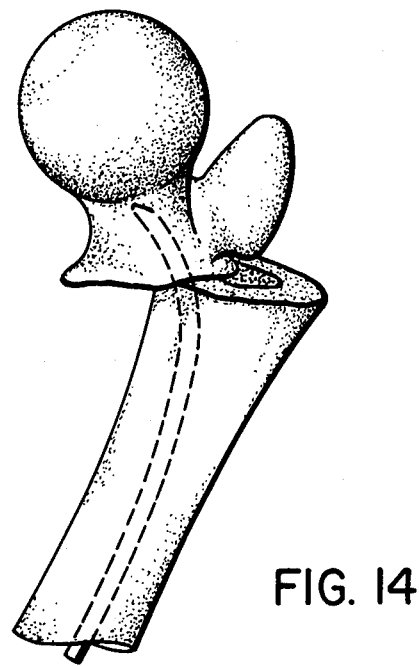
FIGS. 14 and 15 are perspective views showing progress of the nail during the repositioning operation of a leg bone prior to and up to reaching the fixed position shown on FIG. 4.
Figure 15:
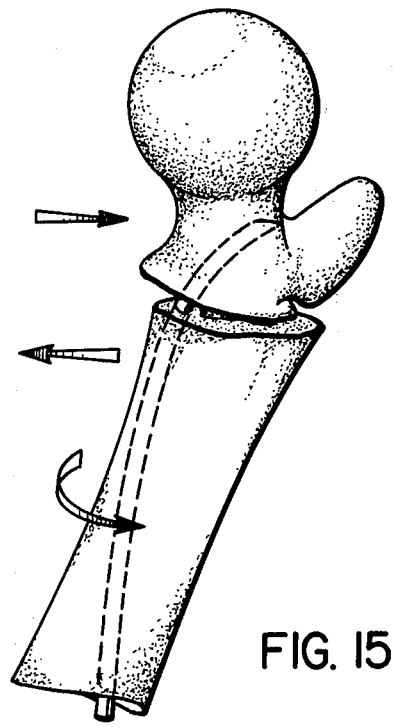

In the embodiment shown in FIG. 12, the steeper curvature $k$ merges into a more gently curved or straight portion $s$. A bend $a$ is succeeded by a straight portion $g$. The end portion is provided with a reverse bend $u$, which is shaped so that it is firmly embraced by the nail set so that the nail can be rotated as it is driven to move the point of the nail to the desired point of the head-neck fragment. This is shown on FIGS. 14 and 15.

FIG. 13 shows different transverse sectional views Qu 1, Qu 2, and Qu 3.

The length of the nails depends on the length of the bone to be fixed. The curvature of the nail is selected so that as it is driven from the medial condyle. It will find virtually by itself the way into the head-neck fragment. The proportional extent of the curvature is desirably similar in nails of all lengths. Together with a properly selected elasticity, the curvature ensures that the nail is straightened as it is driven through the medullary canal and an initial stress is thus imparted to the nail. Owing to this initial stress, the point of the nail can exert a spring force so that the point of the nail can enter even substantially displaced fragments and can be rotated so that these fragments are displaced to any desired position and thus repositioned. This is shown on FIGS. 14 and 15.

When the fragments have thus been repositioned, the nail is driven further toward the cranial portion.

Figures 16, 17:
FIGS. 16 and 17 are X-ray views corresponding to FIG. 4.

Under the spring force, the nail then bends in the enlarged portion of the trochanterous region into the angled femur neck. This is shown in FIGS. 16 and 17.

The nail may be provided with a coating of plastics material, particularly teflon. Such sliding layer will avoid a fretting corrosion, to which even high-grade material is susceptible.

Figure 3:
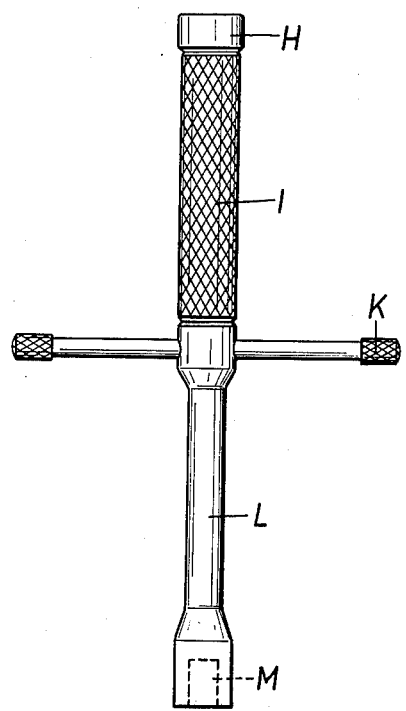
FIG. 3 shows a corresponding nail set.

The nail set shown in FIG. 3 has a portion L, which is formed with a recess M, which exactly conforms to the flattened end portion F of the nail. The portion L is succeeded by a knurled handle I, which is succeeded by a head H, which is struck by the hammer for driving the nail. A cross-member K, which is knurled at its ends, serves to rotate the nail set and the nail.

The portion L of the nail set may be angled to facilitate the access to the nail and to enable a cranklike action.

The nail can be pulled out of the bone by means of a hook, which is hooked into the slot G.

Figure 4:
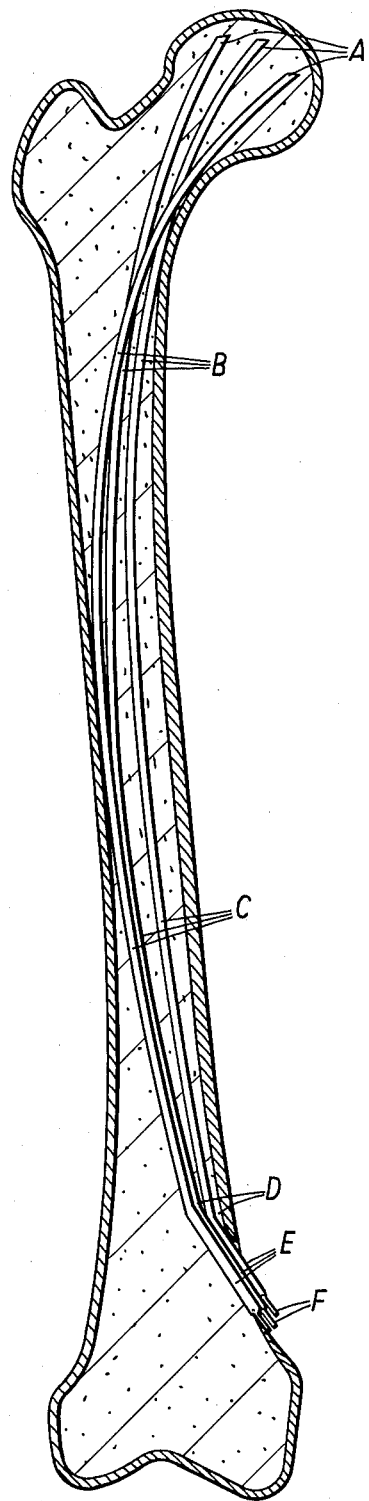
FIGS. 4 and 5 are, respectively, a transverse sectional view showing a bone into which three nails according to FIGS. 1 and 2 have been driven.
Figure 5:
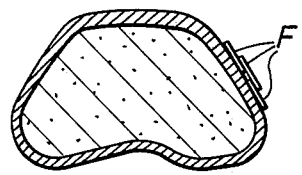

FIG. 4 shows how the driven nails extend in the bone. It is apparent from FIG. 5 that the flattened end portions F can easily be accommodated one beside the other or one over the other so that they require little space and the restrictions regarding the knee joint are reduced.

Other embodiments of the nail set according to the invention will be described hereinafter.

Figure 6:
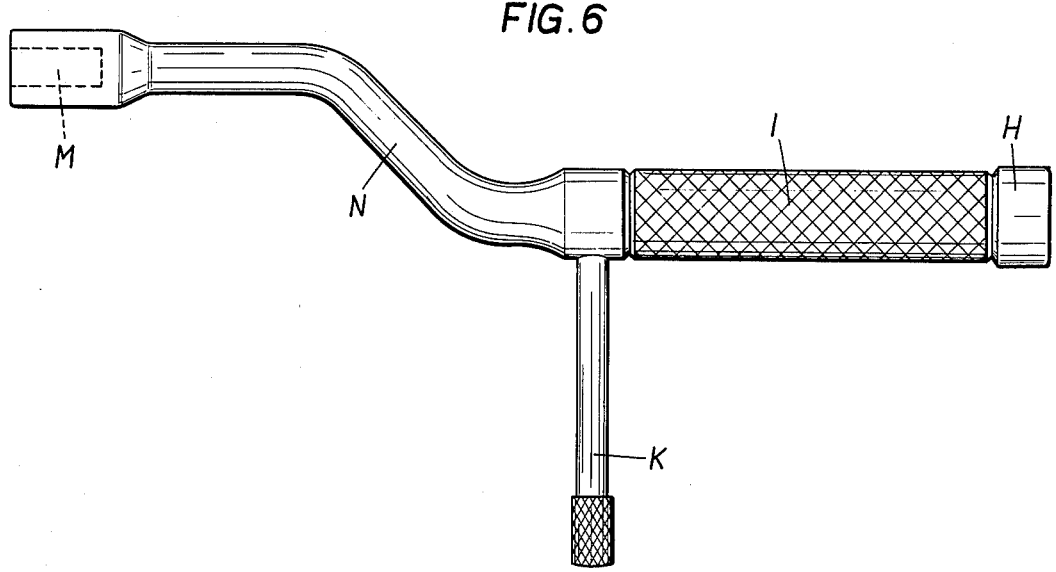
FIG. 6 is an enlarged front elevation showing a second embodiment of the nail set.

FIG. 6 shows a nail set N, which has also a recess M and which is crank-shaped and provided with a handle I and a transverse member K. Owing to its crank shape, the nail set can be rotated and with it the nail. The head H is again struck by the hammer.

Figure 7:
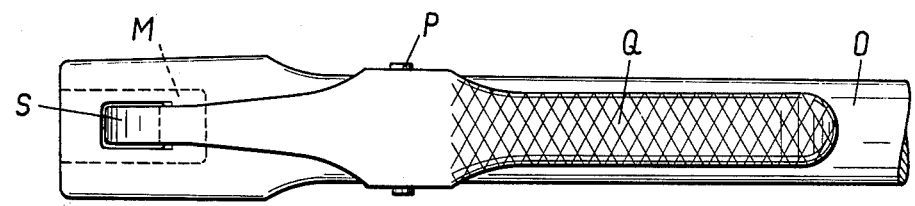
FIGS. 7 and 8 are enlarged views showing as a top plan view and a front elevation, respectively, a third embodiment of the nail set.
Figure 8:
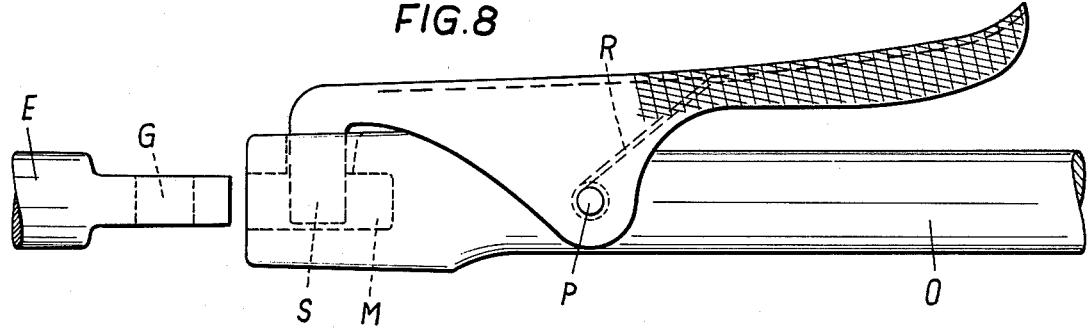

The nail set O shown in FIGS. 7 and 8 comprises a lever Q, which is pivotally movable on the axis P against the force of a spring R, which is wound around the axis P. The lever Q terminates in a hook S, which can extend through a bore into the recess M, which receives the flattened end of the nail portion E. That end is provided with an aperture G.

When the handle of the lever Q is depressed, the hook S of the lever is retracted from the recess M so that porion F can be pushed into the recess M. When the lever Q is released, the hook S then springs into the aperture G.

Figure 10:
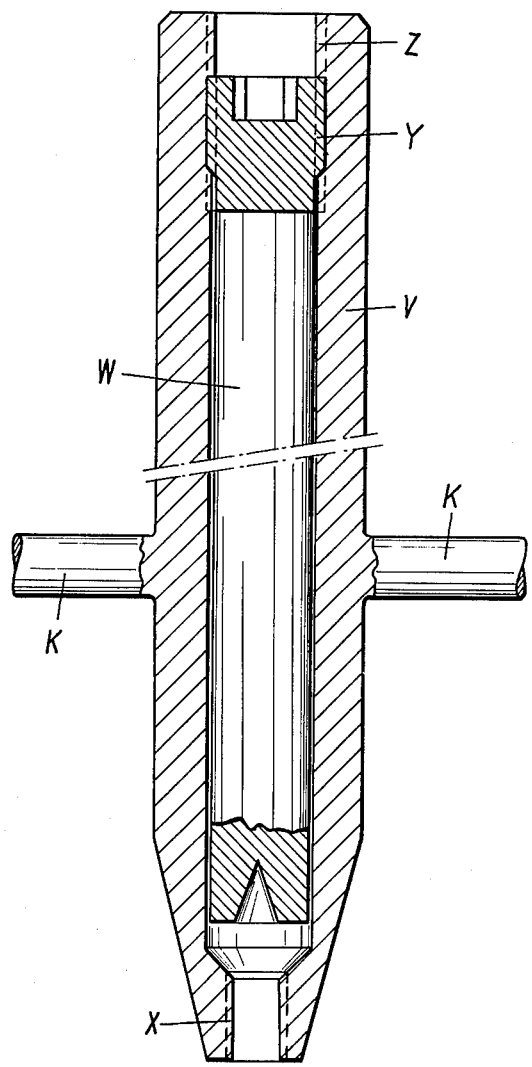
FIG. 10 is an enlarged longitudinal sectional view showing a fourth embodiment of a corresponding nail set.
Figure 9:
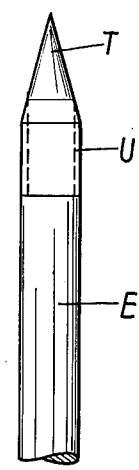
FIG. 9 is an enlarged side elevation showing the rear end of the nail.

In the embodiment shown in FIGS. 9 and 10, the nail portion E has a conical point T and screw threads U. The nail set V has a longitudinal bore, in which a cylindrical element W is slidable. When the screw threads U have been screwed into the tapped bore X of the nail set V, an Allen-head screw Y having a hexagonal or square recess may be screwed into a tapped bore Z to force the cylindrical portion W against the cone T to hold the nail in position. The nail set V is also provided with transverse members K.

The nail sets shown in FIGS. 6 and 7, 8 and 10 may be used to drive the nail into and to pull it out of the bone.

What is claimed is:

1. A curved nail for repositioning and fixing fragments of bones, such as leg bones from below and permitting rotational elastic penetration of its proximally-driven end into the upper portion of the bone, such as the femur head comprising:
    a proximal end,
    a curved relatively thin, flexible and resilient portion extending from said proximal end,
    a distal end provided with a coupling element adapted to be connected to means for driving the nail, said nail being straightened as it is driven through the medullary canal, and an initial stress being thus imparted to it, and
    a straight portion between said coupling element and said curved portion.

2. A nail as set forth in claim 1, which comprises a bend between said distal end and said straight portion, the proportional extent of the curvature of the said curved elastic portion conforming to the femur condyle.

3. A curved nail for repositioning and fixing fragments of bones, which nail comprises, a proximal end, a curved portion extending from said proximal end, a distal end provided with a coupling element adapted to be connected to means for driving the nail, a first straight portion between said coupling element and said curved portion, a first bend between said distal end and said first straight portion, and a second straight portion between said distal end and said first bend.

4. A nail as set forth in claim 3, which comprises, a second bend between said second straight portion and said distal end, and a third straight portion between said second bend and said distal end.

5. A curved nail for repositioning and fixing fragments of bones, which nail comprises
    a proximal end,
    a curved portion extending from said proximal end,
    a distal end provided with a coupling element adapted to be connected to means for driving the nail,
    a straight portion between said coupling element and said curved portion, and
    a second curved portion, which is adapted to conform to a femur condyle and is disposed between said straight portion and said distal end.

6. A nail as set forth in claim 1, which comprises
    a polygonal portion terminating at said distal end and
    a portion which adjoins said polygonal portion and is aligned therewith.

7. The combination comprising a curved nail for repositioning and fixing fragments of bones and a nail set for use in driving such nail,
    said nail having a rear end portion formed with a conical tip and with screw threads,
    said nail set having a longitudinal bore, which has a first tapped portion adapted to threadedly engage said screw threads of said nail, and a second tapped portion axially spaced from said first tapped portion, said nail set comprising an Allen-head screw screwed into said second tapped portion, and a cylindrical member disposed in said longitudinal bore and engaging said Allen-head screw and said rear end portion of said nail and non-rotatably connecting the latter to said nail set.

8. The combination comprising a curved nail for repositioning and fixing fragments of bones and a nail set for driving said nail, said nail comprising a proximal end, a curved portion extending from said proximal end, said nail being relatively thin, flexible and resilient so that it is straightened as it is driven through the medullary canal and an initial stress being thus imparted to it, a distal end provided with a coupling element, and a straight portion between said coupling element and said curved portion, said nail set comprising a shank, which is formed at one end with a recess conforming to and receiving said coupling thereto, and a transverse member connected to said shank at a point spaced from said one end.

* * * * *